(12) United States Patent
Le Huec et al.

(10) Patent No.: US 7,052,502 B2
(45) Date of Patent: May 30, 2006

(54) MEDICAL INSTRUMENT AND METHOD FOR CREATING A CAVITY FOR ENDOSCOPIC INTERVENTION

(75) Inventors: Jean Charles Le Huec, Pessac (FR); Christophe Lafond, Bellerive sur Allier (FR)

(73) Assignee: Karl Storz GmbH & Co. KG (DE)

( * ) Notice: Subject to any disclaimer, the term of this patent is extended or adjusted under 35 U.S.C. 154(b) by 261 days.

(21) Appl. No.: 10/067,412

(22) Filed: Feb. 5, 2002

(65) Prior Publication Data

US 2002/0156433 A1 Oct. 24, 2002

Related U.S. Application Data

(63) Continuation of application No. PCT/EP00/07269, filed on Jul. 28, 2000.

(30) Foreign Application Priority Data

Aug. 5, 1999 (DE) ................................ 199 37 043

(51) Int. Cl.
*A61B 17/50* (2006.01)
*A61B 17/24* (2006.01)
*A61F 11/00* (2006.01)

(52) U.S. Cl. .................... 606/127; 606/114; 606/108

(58) Field of Classification Search ................ 606/113, 606/114, 198, 180, 108–127, 147; 604/264; 600/564

See application file for complete search history.

(56) References Cited

U.S. PATENT DOCUMENTS

| | | | |
|---|---|---|---|
| 4,909,789 A | 3/1990 | Taguchi et al. | 604/107 |
| 5,064,428 A * | 11/1991 | Cope et al. | 606/127 |
| 5,351,679 A | 10/1994 | Mayzels et al. | 128/20 |
| 5,402,772 A | 4/1995 | Moll et al. | 128/20 |
| 5,441,044 A | 8/1995 | Tovey et al. | 600/234 |
| 5,632,746 A | 5/1997 | Middleman et al. | 606/78 |
| 5,735,289 A * | 4/1998 | Pfeffer et al. | 606/113 |
| 5,803,902 A | 9/1998 | Sienkiewicz et al. | 600/203 |
| 5,891,153 A * | 4/1999 | Peterson | 606/107 |
| 5,964,771 A * | 10/1999 | Beyar et al. | 606/108 |
| 6,174,318 B1 * | 1/2001 | Bates et al. | 606/127 |

FOREIGN PATENT DOCUMENTS

| | | |
|---|---|---|
| DE | 640 126 | 12/1936 |
| DE | 82 16 373.1 | 9/1982 |
| DE | 43 18 950 | 9/1994 |
| DE | 196 05 615 | 8/1997 |
| EP | 0 512 729 | 11/1992 |
| EP | 0 705 566 | 4/1996 |

* cited by examiner

*Primary Examiner*—Nicholas D. Lucchesi
*Assistant Examiner*—Roz Maiorino
(74) *Attorney, Agent, or Firm*—St. Onge Steward Johnston & Reens LLC

(57) ABSTRACT

The invention relates to a medical instrument for creating a cavity for an endoscopic intervention in a human or animal body, comprising a hollow cylindrical encasing trocar tube which can be inserted into an artificial body opening and an expander which can be extracted from and retracted into said tube. The above-mentioned medical instrument consists of a small number of parts and is easy to handle. It is characterized in that the expander comprises a retaining element which is arranged outside the trocar tube in addition to at least two spring blades which are made of a flexible material and form an arc in the respective median sections thereof, whereby the two ends thereof are respectively fixed to the retaining element, extending through the tube of the trocar. The invention also relates to a method for the use of said medical instrument.

10 Claims, 2 Drawing Sheets

MEDICAL INSTRUMENT AND METHOD FOR CREATING A CAVITY FOR ENDOSCOPIC INTERVENTION

This application is a continuation of pending International Application PCT/EP00/07269 filed on Jul. 28, 2000, which designates the United States and claims priority from German Application 199 37 043 filed on Aug. 5, 1999.

FIELD OF THE INVENTION

The invention relates to a medical instrument for creating a cavity for an endoscopic intervention in a human or animal body, comprising a hollow cylindrical encasing trocar tube which can be inserted into an artificial body opening and an expander which can be extracted from and retracted into said tube. The invention also relates to a method for the use of said medical instrument.

Typically, the abdominal cavity, for example, is inflated with a suitable gas for endoscopic intervention so as to create sufficient operating space for the surgeon. Access for medical instruments is created by a valve through one or more trocars. This type of endoscopic intervention proved to be useful in practice; however, vigilance must be exercised to ensure that the area around the trocar is sealed off well, and to ensure a uniform regulation and control of pressure.

Apart from this method of surgery where a cavity for the intervention is created by gas, various medical instruments are known for creating a sufficient operating space by mechanical means. Compared to the use of gas, mechanical expanders have the obvious advantage not just of creating a cavity for surgery, but also make it possible to specifically press individual organs or portions of tissue away from the surgical area.

A medical gripping instrument of the aforementioned type has been established in U.S. Pat. No. 5,351,679 A. The medical instrument disclosed therein comprises an expander consisting of three fan-shaped metal blades capable of expanding, and which are connected with each other at their ends by way of articulated crossbars. This type of instrument allows the tissue to be kept away from the surgical area; however, with its flat operating expander the instrument does not allow for the creation of an unobstructed space for surgery. In addition there is the risk of tissues being caught between the metal blades when they are folded up.

A further device which can be inserted into the body has been established in U.S. Pat. No. 5,402,772. This device is inflated inside the body by means of a liquid or gas to create the necessary space for surgery. However, because a pressure medium must be introduced and monitored, use of this known device also is very cumbersome and expensive. Moreover, the material used for the inflation is difficult to clean sufficiently for a second use, so this method involves a costly medium for one-time use.

Another tissue-expanding device for creating a cavity for endoscopic access has been disclosed in DE-C1-43 18 950. This known device consists of a shaft which can be inserted through a standard-type trocar into the body and whose proximal end is provided with a grip, whereas individual elastic spring blades are fixed on its distal end. These blades can be contracted by means of a stretching device activated by said grip in order to form a cavity. The drawback of this known expander is the complex and multipartite structure of the stretching device, which must be completely disassembled for thorough cleaning after each use.

On the basis of current technology, the present invention's objective is to provide a medical instrument for creating a cavity for an endoscopic intervention, which is made up of a small number of component parts and which ensures easy manipulation.

The solution to this objective is characterized in that the expander, which is made up of a retaining element affixed outside the trocar tube in addition to at least two spring blades made of a flexible material. These spring blades each form an arc in their middle section. Both ends, extending through the tube of the trocar, are fixed to the retaining element.

The medical instrument of this invention is distinguished in that it consists of few component parts: the trocar tube, the retaining element, and the spring blades. When the spring blades, which are fixed on the retaining element with both of their ends, are bent so that they form an arc, they immediately and automatically expand after emerging from the trocar tube, so that none of the expanders available from contemporary technology will be necessary. The inventive expander allows the formation of a spatial cavity for intervention.

In accordance with a practical embodiment of the invention, it is suggested that the trocar tube consists of two coaxially arranged sleeves positioned at a distance to each other, whereby the spring blades fixed in said retaining element extend through the gap formed between the coaxial sleeves. The advantage of this design is that the instrument is formed of a single part, and moreover the expander does not need to be inserted into the trocar tube since the spring blades are positioned within the double-walled trocar tube.

To create a spatially expanded cavity, the position of the spring blades (at least two) on the retaining element is shifted, so that the planes set by the arcs are intersecting. A maximum-sized cavity is obtained for endoscopic intervention when two spring blades are fixed at an angle of 90° to each other on the retaining element. This arrangement forms a spherical cavity where the arcs of the two spring blades intersect at 90° angle.

In accordance with a practical embodiment of the invention, it is suggested that the expander consists of four spring blades fixed on the retaining element. These blades should be arranged at an angle of 45° to each other on said retaining element. These eight arms of the four spring blades—bent in an arc shape—are particularly effective at keeping the non-operative tissue away from the surgical area. At the same time sufficient space is left between the individual arms of the spring blades for insertion of a surgical instrument into the cavity that is formed.

In accordance with a practical embodiment of this invention, it is suggested that the individual arcs of the spring blades are connected through their vertices by means of a common element in order to prevent any shifting of the individual arcs of the spring blades against each other.

TiNi, a titanium and nickel alloy, is a flexible and durable material commonly used in biomedical applications. TiNi is the preferred material for the spring blades, although other flexible and durable material may be used as well.

The versatility of the inventive medical instrument can be further extended by providing the retaining element with a central opening through which, one or more medical instruments can be inserted into the body. The medical instrument can be an endoscope, gripping pincer, scissors, an HF instrument, or a suction/rinsing tube. This embodiment is especially advantageous, since the instrument inserted through the expander will automatically be positioned immediately within the artificially created cavity.

In accordance with a further development of the inventive medical instrument, a locking device can be fixed on the retaining element to permit the expander to be locked in the fixed position in which it was inserted into the trocar tube.

The inventive procedure for the use of the medical instrument for creating a cavity in a human or animal body for endoscopic surgery is characterized by the following steps:

a) inserting the trocar tube into an artificial body opening;

b) inserting the expander through said trocar tube until the spring blades are projecting from its distal end to expand in the form of an arc so as to create a cavity for an endoscopic intervention;

c) retracting the expander through the trocar tube after the endoscopic intervention, and extracting the trocar tube from the artificial body opening.

As mentioned above, handling of the inventive medical instrument is particularly simple since it is used in the same way as a normal surgical instrument inserted into the body through the trocar tube and no other measures are necessary to bring the spring blades into position to form the cavity.

In accordance with a preferred embodiment for the use of the present invention, a further medical instrument is inserted through the retaining element and through the trocar tube into the cavity formed by the spring blades (see step b).

Finally, the invention suggests that the depth of insertion of the expander into the trocar tube is fixed after inserting the expander through the trocar tube and after forming the cavity by means of the spring blades.

BRIEF DESCRIPTION OF THE DRAWINGS

The appended drawings depict an example of the preferred embodiment of a medical instrument for creating a cavity. Further features and advantages of the present invention are defined. The drawings are as follows.

DETAILED DESCRIPTION OF THE DRAWINGS

Figure 1:
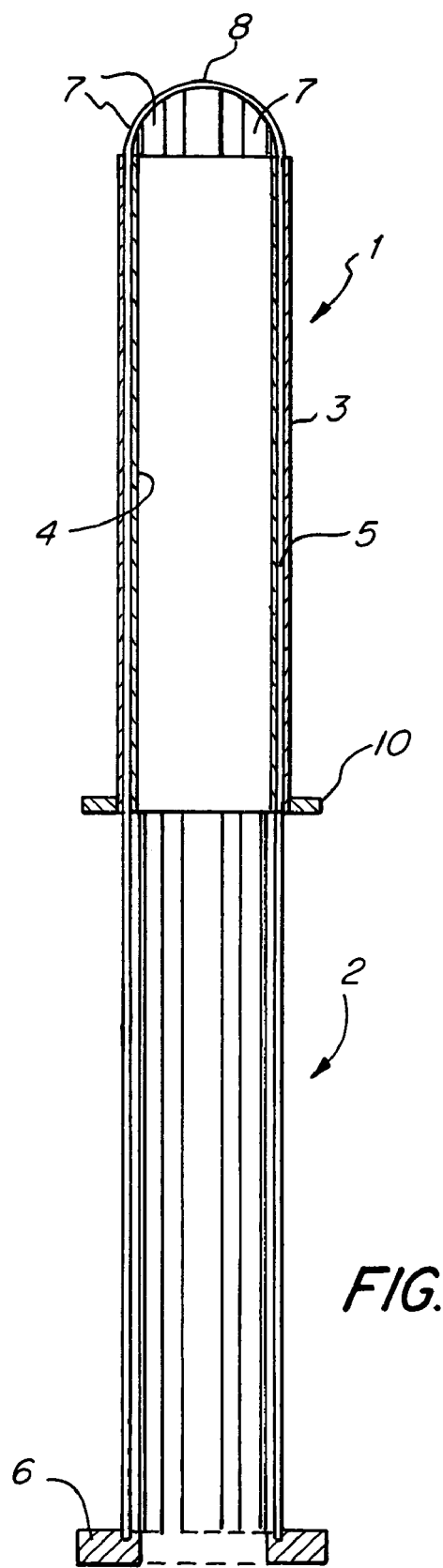
FIG. 1 A schematic and partly sectional side view of the medical instrument, with the spring blades contracted.
Figure 2:
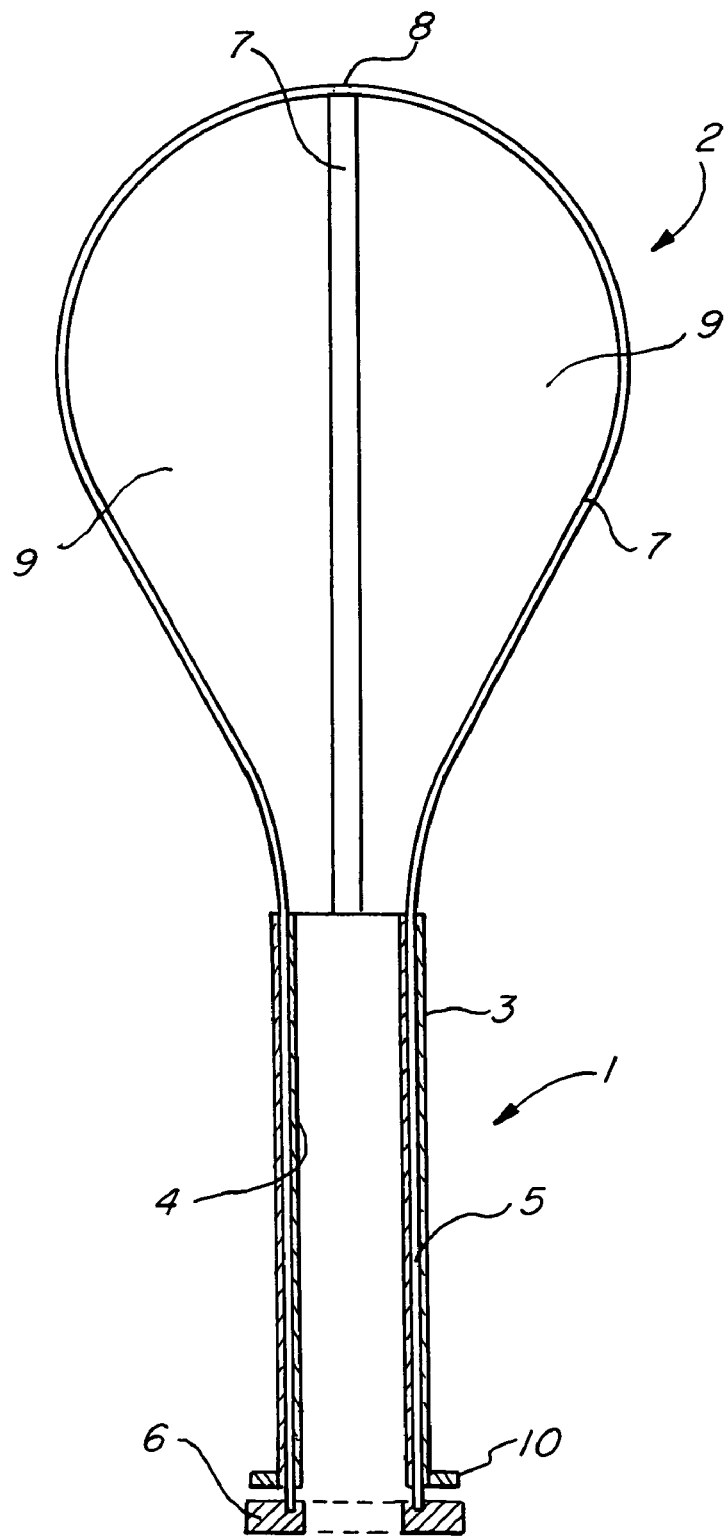
FIG. 2 A view as shown in FIG. 1, where the spring blades are in operating position.

The medical instrument shown in FIGS. 1 and 2 basically consists of a trocar tube 1 and an expander 2 which can be inserted into said tube 1.

In the example of the preferred embodiment, the trocar tube 1 consists of an outer sleeve 3 and an inner sleeve 4 positioned coaxially in the outer sleeve 3, where the outer sleeve 3 and inner sleeve 4 are positioned at a distance to form a gap 5.

The expander 2, on the other hand, is made up of a retaining element 6 fixed on its proximal end and four spring blades 7 fixed on the retaining element 6 as shown by the example of the embodiment. As depicted in FIG. 2, each spring blade 7 is fixed at both ends to the retaining element 6 to form an arc, and arranged to the next spring blade 7 in a way that the planes set by the arcs are intersecting. To prevent a mutual displacement of the intersecting arcs of the spring blades 7, the spring blades 7 are connected by means of a common connecting element 8 by the vertices of their arcs. Furthermore, the figures show that in the present embodiment the spring blades 7 are extending through the gap 5 between the inner sleeve 4 and the outer sleeve 3 of the trocar tube 1 if seen from the retaining element 6.

The medical instrument described herein is used and operated as follows:

To insert the medical instrument into a human or animal body, the trocar tube 1 is first shifted to the distal end of the expander 2, as shown in FIG. 1. When said trocar tube 1 is shifted in this direction, the flexible spring blades 7 are compressed in such a way that the outer diameter on the distal end of the expander 2 no longer exceeds the outer diameter of said trocar tube 1.

Figure 3:
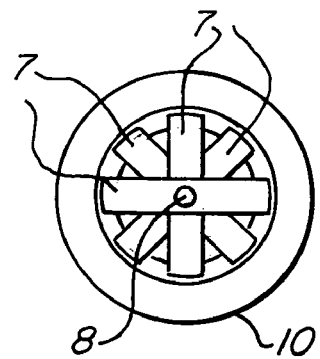
FIG. 3 An aerial view of the instrument shown in FIG. 1 from its distal end.

Subsequently, the trocar tube 1 is inserted into an artificial body opening, and then the expander 2 is pressed through said trocar tube 1 by means of the retaining element 6 until the spring blades 7 are again projecting again from the gap 5 of said trocar tube 1 and are formed into the shape shown in FIG. 2 thanks to the elasticity of the material. In said shape shown in FIG. 2, where the spring blades 7 are shifted toward one another on the retaining element 6, a spherical cavity is formed for the endoscopic intervention. For purposes of clarity, FIG. 2 shows only two spring blades 7, shifted to one another at an angle α, equal to 90°. FIGS. 1 and 3 show that four spring blades 7 shifted to each other at an angle of 45° are fixed on the retaining element 6.

After the endoscopic intervention, during which one or more surgical instruments, are inserted through the window—formed between the individual arms of the spring blades 7—into the cavity formed by the expander 2, the expander 2 is retracted by means of the retaining element 6 into the trocar tube 1 so that the spring blades 7 are folded up again, as shown in FIG. 1. Thereafter, the trocar tube 1 is extracted from the artificial body opening. A peripheral rim 10 on the proximal end of the trocar tube 1 is used for gripping and shifting.

Thus the remarkable feature of the medical instrument in accordance with the present invention is its structure comprising only a few component parts, as well as its particularly simple mode of intervention.

| Key | |
|---|---|
| 1 | Trocar tube |
| 2 | Expander |
| 3 | Outer sleeve |
| 4 | Inner sleeve |
| 5 | Gap |
| 6 | Retaining element |
| 7 | Spring blade |
| 8 | Connecting element |
| 9 | Window |
| 10 | Rim |

What is claimed is:

1. Medical instrument for creating a cavity for an endoscopic intervention in a human or animal body, comprised of a hollow cylindrical encasing trocar tube which can be inserted into an artificial body opening and an expander which can be extracted from and retracted into said trocar tube, characterized in that the expander comprised of a retaining element arranged outside the trocar tube in addition to at least two spring blades which are made of a flexible material and form an arc in the respective middle sections, whereby said at least two spring blades are shifted toward one another on the retaining element in such a way that the plane surface created by the arcs are intersecting and the two ends of each blade are fixed to the retaining element, extending through the tube of the trocar, wherein the trocar tube comprises two coaxial sleeves arranged one inside of the other and at a distance to one another, an outer one of the two coaxial sleeves having a generally cylindrical inner surface and an inner one of the coaxial sleeves having a generally cylindrical outer surface, the inner surface of the outer sleeve and the outer surface of the inner sleeve defining a generally annular gap, the generally annular gap extending substantially along a length of the trocar, and wherein the spring blades fixed in said retaining element extend through the annular gap formed between said coaxial sleeves.

2. Medical instrument in accordance with claim 1, characterized in that two spring blades are fixed on the retaining element in a way that they are shifted to one another at an angle of 90°.

3. Medical instrument in accordance with claim 1, characterized in that the expander consists of four spring blades fixed on the retaining element in such a way that they are shifted at an angle of 45°.

4. Medical instrument in accordance with claim 1, characterized in that the individual arched spring blades are connected with one another on their vertices by means of a common connecting element.

5. Medical instrument in accordance with claim 1, characterized in that the spring blades are made of elastic TiNi.

6. Medical instrument in accordance with claim 1, characterized in that the retaining element is provided with a central opening for inserting at least one additional medical instrument.

7. Medical instrument in accordance with claim 1, characterized in that a locking device on the retaining element is used for fixing the expander into the respective position when inserted in the trocar tube.

8. Method for the use of the apparatus in claim 1, comprising the following steps:

a) Inserting the trocar tube into an artificial body opening, b) Inserting the expander through the trocar tube until the spring blades are projecting from the distal end of said trocar tube and extending again in a way that they form an arc so as to create a cavity for an endoscopic intervention.

c) Retracting the expander through the trocar tube after the endoscopic intervention, d) Extracting the trocar tube from the artificial body opening.

9. Method in accordance with claim 8, wherein, the step of inserting the expander through the trocar tube until the spring blades are projecting from the distal end of said trocar tube and extending again in a way that they form an arc so as to create a cavity for an endoscopic intervention further comprises the step of:

Inserting an additional medical instrument through the retaining element and the trocar tube into the cavity formed by the spring blades.

10. Method in accordance with claim 8, wherein, the step of inserting the expander through the trocar tube until the spring blades are projecting from the distal end of said trocar tube and extending again in a way that they form an arc so as to create a cavity for an endoscopic intervention further comprises the step of:

Fixing the insertion depth of the expander in the trocar tube after forming the cavity by the spring blades.

* * * * *